United States Patent
Labeille et al.

(10) Patent No.: US 6,667,066 B2
(45) Date of Patent: Dec. 23, 2003

(54) **MULTI-ENZYME PRODUCT WITH GLUCOAMYLASE, PROTEOLYTIC AND XYLANASE ACTIVITIES AND METHOD FOR PRODUCING SAME BY SOLID STATE FERMENTATION OF WHEAT BRAN WITH *ASPERGILLUS NIGER***

(75) Inventors: Pierre Jean Labeille, Reims (FR); Jean-Luc Alain Guy Baret, Veneux les Sablons (FR); Francis Lucien Duchiron, Reims (FR)

(73) Assignee: Gie Agro Industrie, Romilly sur Seine (FR)

(*) Notice: Subject to any disclaimer, the term of this patent is extended or adjusted under 35 U.S.C. 154(b) by 0 days.

(21) Appl. No.: 09/910,735

(22) Filed: Jul. 24, 2001

(65) Prior Publication Data

US 2002/0037342 A1 Mar. 28, 2002

Related U.S. Application Data

(63) Continuation of application No. PCT/FR00/00163, filed on Jan. 25, 2000.

(30) Foreign Application Priority Data

Jan. 25, 1999 (FR) .............................................. 99 00775

(51) Int. Cl.⁷ .......................... A23L 1/105; C12N 11/18
(52) U.S. Cl. ............................. 426/31; 426/60; 435/175
(58) Field of Search .............................. 426/31, 60, 61, 426/2; 435/256.1, 256.8, 205, 175, 178

(56) References Cited

U.S. PATENT DOCUMENTS 3,151,983 A * 10/1964 Ely et al. .......................... 99/4

FOREIGN PATENT DOCUMENTS

| SU | 489787 | * | 2/1976 |
| SU | 988867 | * | 10/1983 |
| WO | 94/18306 | | 8/1994 |

OTHER PUBLICATIONS

Labeille & Duchiron, "Glucoamylase production by *Aspergillus niger* in Solid–State Fermentation of Wheat Bran"; Doctoral Thesis, University de Reims, Mar. 1997. (abstract).*

Labeille et al.; Comparative Study of wheat flour sacharification and ethanol production with two glucoamylase preparations; Industrial Crops and Products, vol. 6, No. 3–4, 1997, p.291–295.

Abraham et al.; Development of an Alternate Route for the Hydrolysis of Cassava Flour; Starch Starke; vol. 41, No. 12, 1989, p. 472–476.

Han et al.; Saccharification and Ethanol Fermentation from Uncooked Starch using *Aspergillus niger* Koji; Korean Journal of Food Science and Technology, vol. 17, No. 4, 1985, p.258–264.

Gowthaman et al.; Gas Concentration and Temperature Gradients in a Packed Bed Solid–State Fermentor; Biotechnol. Adv.; 1993, 11(3), p. 611–620.

Stachovicz et al.; Preliminary selection of mould strains producing proteolytic enzmes in submerged cultures; 74–3–08–10602, XP–002119207, 1974.

ATCC Filamentous Fungi Nineteenth Edition, 1996, p. 52, XP–002119206; left–hand column, paragraph 4.

Durand et al.; Solid state fermentations: an attractive alternative to submerged–liquid fermentations; Agro–Food Industry Hi–Tech; 1997, p. 39–42.

Bernfeld; Methods in Enzymology, 1, 149–159, 1955.

Protein Purification Methods—Practical Approach; Harris et al., IRL–Press, Oxford Univesity Press, 1–66, 1989.

Veldman, A. and H. A. Vahl (1994) "Xylanase in Broiler Diets with Differences in Characteristics and Content of Wheat", British Poultry Science, vol. 35, pp. 537–550.

* cited by examiner

*Primary Examiner*—Keith Hendricks
(74) *Attorney, Agent, or Firm*—Jacobson Holman PLLC

(57) ABSTRACT

The invention concerns a multi-enzyme product with glucoamylase, proteolytic and xylanase activities, characterized in that it consists of wheat bran fermented with an *Aspergillus niger* strain, said enzymatic glucoamylase, proteolytic and xylanase activities being present in the following minimum values: glucoamylase activity: at least 100 UG per gram of dry matter; proteolytic activity: at least 100 UP per gram of dry matter; xylanase activity: at least 100 UX per gram of dry matter, provided that at least one of the following conditions is satisfied: the gluycoamylase activity is at least 750 UG per gram of dry matter, or the xylanase is at least 300 UX per gram of dry matter. The invention is useful for producing ethanol or monogastric animal feed.

15 Claims, No Drawings

MULTI-ENZYME PRODUCT WITH GLUCOAMYLASE, PROTEOLYTIC AND XYLANASE ACTIVITIES AND METHOD FOR PRODUCING SAME BY SOLID STATE FERMENTATION OF WHEAT BRAN WITH *ASPERGILLUS NIGER*

This application is a continuation of International PCT application no. PCT/FR00/00163, filed on Jan. 25, 2000, which designated the United States.

FIELD OF THE INVENTION

The invention relates to a multi-enzyme product with glucoamylase, proteolytic and xylanase activities and a method for producing same by solid state fermentation of wheat bran with *Aspergillus niger*.

BACKGROUND OF THE INVENTION

It is known to produce ethanol from corn starch by an enzymatic method comprising a stage for liquefying the starch with an alpha-amylase for hydrolyzing the starch to dextrins, and then a saccharification stage by a glucoamylase (also called amyloglucosidase) for hydrolyzing the dextrins to glucose, and finally a stage for fermenting the latter to ethanol.

The use of alpha-amylase and glucoamylase enzymes is generally satisfactory when relatively pure starch milk, obtained by the wet milling of corn, is used as starting material, but when it is desired to substitute wheat starches or wheat flours for corn starch, no satisfactory results are obtained with these two enzymes alone because of the presence of hemicelluloses, which increase the viscosity of the saccharified flour worts to the extent that this creates a problem for carrying out the method. It is necessary to use, at the saccharification stage, auxiliary enzymes such as cellulases and hemicellulases in order to reduce the viscosity and remedy this problem. Moreover, it is desirable also to use proteases during saccharification so as to hydrolyze the proteins in the flour and thus enrich the wort with soluble nitrogen in anticipation of the subsequent alcoholic fermentation stage. The traditional supply of nitrogen source necessary for the growth of yeasts during this fermentation may thus be reduced.

All these enzymes are individually commercially available in purified form, but have the disadvantage of being relatively expensive and therefore of increasing the cost of producing ethanol from wheat. In addition, compositions have to be formulated from individual enzymes, which complicates the method.

A need therefore exists for an inexpensive multi-enzyme product combining glucoamylase, proteolytic and hemicellulase activities to produce ethanol from wheat flours at a low cost.

The invention aims to satisfy this need.

SUMMARY OF THE INVENTION

The present invention relates to a multi-enzyme product exhibiting glucoamylase, proteolytic and xylanase activities, characterized in that it consists of wheat bran fermented with an *Aspergillus niger* strain, said enzymatic glucoamylase, proteolytic and xylanase activities being present at the following minimum values:
glucoamylase: at least 100 GU per gram of dry matter,
proteolytic: at least 100 PU per gram of dry matter,
xylanase: at least 100 XU per gram of dry matter, provided that at least one of the following conditions is satisfied:

the glucoamylase activity is at least 750 GU per gram of dry matter the xylanase activity is at least 300 XU per gram of dry matter.

The glucoamylase activity is preferably at least 1 500 GU per gram of dry matter and/or the xylanase activity is at least 400 XU per gram of dry matter.

Also, the proteolytic activity is preferably at least 400 PU per gram of dry matter.

The invention also relates to a method of producing this multi-enzyme product, characterized in that it comprises the stages consisting in (a) taking wheat bran; (b) moistening and heat-treating said bran so as to pasteurize it or sterilize it; (c) inoculating the resulting wheat bran with an *Aspergillus niger* strain; (d) the bran being in the form of a layer at least 10 cm thick, fermenting it in the solid state in a reactor which is aerated and stirred periodically for a period of 1 to 3 days, at a temperature of 28–38° C., preferably 32 to 36° C., said bran being adjusted to an initial moisture content of 50 to 60 wt. % which is substantially maintained during the duration of the fermentation, under aeration conditions appropriate for avoiding accumulation of carbon dioxide which is harmful to the fermentation in the reactor and a rise in temperature due to fermentation above the recommended range, until the fermentation product exhibits the following minimum enzyme activity values:
glucoamylase: at least 100 GU per gram of dry matter,
proteolytic: at least 100 PU per gram of dry matter,
xylanase: at least 100 XU per gram of dry matter, provided that at least one of the following conditions is satisfied:

the glucoamylase activity is at least 750 GU per gram of dry matter the xylanase activity is at least 300 XU per gram of dry matter.

The glucoamylase activity is preferably at least 1 500 GU per gram of dry matter and/or the xylanase activity is at least 400 XU per gram of dry matter.

Also, the proteolytic activity is preferably at least 400 PU per gram of dry matter.

The *Aspergillus niger* strain is preferably chosen from the NRRL 3112 strain, the ATCC 76061 strain and the strains obtained from said strains by selection or mutation when a high glucoamylase activity is desired. The ATCC 76061 strain is particularly preferred.

DETAILED DESCRIPTION

When a high glucoamylase activity is desired, the wheat bran used as starting material should be a non-starch-free bran. Apart from this restriction, any bran may be used. However, the bran preferably comprises a significant proportion (at least 40 wt. %) of particles of less than 1 mm.

The characteristics of two suitable brans are given below by way of illustration.

|  | Bran A | Bran B |
|---|---|---|
| Characteristics |  |  |
| Moisture (%) | 12.3 | 19.5 |
| Protein content (% WM*) | 13.8 | 14.8 |
| Starch content (% WM*) | 24.6 | 21.3 |
| Particle size |  |  |
| >1.25 mm | 53.9 | 0.7 |
| from 1.0 to 1.25 mm | 8.1 | 1.3 |

-continued

|  | Bran A | Bran B |
|---|---|---|
| from 0.5 to 1.0 mm | 33.3 | 68.2 |
| from 0.25 to 0.5 mm | 3.7 | 24.6 |
| from 0.16 to 0.25 mm | 0.3 | 2.6 |
| <0.16 mm | 0.7 | 2.6 |

% WM = % relative to the wet matter.

The wheat bran should be moistened and heat-treated in order to pasteurize it or to sterilize it. It is advantageous that the heat treatment does not precede the moistening because poor fermentation results have been obtained if the bran is heat-treated before moistening. The heat treatment may consist in heating, for example, in an autoclave. An autoclave treatment of 20 min at 120–121° C. has proved highly satisfactory, but less severe conditions (pasteurization at 105° C. for 15 min in an oven) are also suitable. It is also possible to carry out the heat treatment of the bran by injecting steam into it, which may make it possible to moisten the bran simultaneously.

The pH may advantageously be adjusted during moistening in the range from 4 to 5.5 in order to improve the pasteurizing effect of the heat treatment and the initiation of the desired fermentation.

In addition to its sterilizing function, the effect of the heat treatment is to promote gelatinization of the starch contained in the wheat bran and therefore the availability of this substrate for the fungus *Aspergillus niger*, which allows more effective fermentation.

The moistening of the bran is important because the water content influences the performance of the fermentation. The initial water content of the bran is initially adjusted to 50–60%, preferably 50–55%, of the total mass of the bran and of the water and it is substantially maintained in this range during fermentation, for example by periodically supplying water in order to compensate for the loss of water from the medium. The expression "substantially maintained" means that it is acceptable for the moisture level to take a value which varies slightly (±5% units) from the range 50–60% during a relatively brief period between two successive adjustments of the moisture level or at the end of fermentation. It is advantageous, in any case, not to drop below a moisture level of 45%. The moisture level of the culture medium tends to decrease during the culture through evaporation due to the increase in temperature generated by the fungal growth, said medium being a poor heat conductor. The quality of the water used also plays a significant role. Good quality running water or distilled water may be used.

The inoculation of the wheat bran may be performed with any appropriate inoculum. Persons skilled in the art know many ways of preparing a suitable inoculum from a selected strain. The inoculum dose is advantageously at least $1 \times 10^7$ spores/gram of initial dry matter.

The fermentation may be carried out in any appropriate reactor. Examples of a reactor which can be used are those described in the paper by A. DURAND et al., published in Agro-Food-Industry Hi-Tech (May–June 1997, pages 39–42).

The fermentation may be carried out for a period of 1 to 3 days, preferably of 30 to 60 hours. At less than 1 day, the fermentation is too incomplete. After 3 days, the fermentation is complete or practically complete and it would be uneconomical to prolong it further. The temperature of the medium is typically maintained between 28 and 38° C., preferably between 32 and 36° C., which corresponds to the optimum activity range known for the *Aspergillus niger* strains to be used in the invention. For this purpose, the air temperature is advantageously set at 34–38° C. for the first few hours of fermentation in order to promote germination of the spores, and then reduced to 28–32° C. for the remainder of the fermentation in order to contribute to the regulation of the temperature of the medium.

The pH of the fermentation medium is not usually regulated. If its starting value is close to 6.0–6.4, the pH decreases to 3.8–4.2 during culture but increases at the end. This change is generally correlated with the fungus sporulation phase. The variation of the pH constitutes a good indicator of the state of the culture.

The fermentor should be aerated, preferably continuously, in order to supply the oxygen necessary for fermentation and to avoid the excessive accumulation of carbon dioxide produced by fermentation. In addition, the aeration helps to control the temperature and the moisture of the culture medium. The air is preferably substantially saturated with water in order to limit the tendency for the medium to dry out. It is difficult to give quantitative information on the aeration rate because many variables, in particular the size and the geometry of the reactor, the quantity of its load, and the like, come into play. Simple routine trials will allow persons skilled in the art to easily determine a suitable aeration rate in each practical case, however.

The bran load in the fermentor should be periodically added during fermentation using stirring means, such as stirring arms, blades or spatulas, or lead screws so as to avoid the formation of impermeable masses and so that the aeration reaches the entire mass of bran as homogeneously as possible. Excessively vigorous stirring which could harm the fungus should be avoided, however.

The product of the invention is a solid product which is useful in particular for the production of ethanol from wheat. It may be directly added to liquefied starch (dextrins) obtained in the liquefaction stage, in order to carry out the saccharification. For this application, it is the glucoamylase activity which is the most important factor. A product of the invention will therefore preferably be used which has a glucoamylase activity of at least 750 GU, for example, preferably of at least 1 500 GU per gram of dry matter.

Another possible use of the product of the invention relates to the production of wheat-based feed for monogastric animals, for example poultry and pigs. In this application, it is the xylanase activity which constitutes the most important factor. A product will therefore be used in this application which preferably has a high xylanase activity, for example of at least 400 XU per gram of dry matter.

The product of the invention may be dried or frozen for storage, if desired.

The drying should be carried out at a moderate temperature so as not to affect the enzyme activity. Heating in an oven at 40° C. has proved to be appropriate, for example. Freezing may be carried out on the moist product at low temperature, for example at −20° C.

In the examples, the various enzyme activities were measured by the following methods:

a) Glucoamylase activity

The action of a glucoamylase (GA) preparation on a starch solution brings about the release of reducing sugars. Heated at 100° C. in the presence of 3,5-dinitrosalicylic acid (DNS), these compositions take on a brown color which is measured on a spectrophotometer (Kontron Instruments, Milan, Italy) at 540 nm.

The reaction medium contains

| starch solution 1% | 500 µl |
|---|---|
| citrate buffer 0.1 at pH 4.5 | 450 µl |
| enzyme solution: | 50 µl |

The reaction occurs for 30 min at 60° C. (55° C. for the *A. orizae* GAs). Samples are collected every 5 min, mixed with DNS and placed in an ice bath. They are then heated for 5 min at 100° C., rapidly cooled and then assayed at 540 nm.

These assay conditions were established after studying the influence of the temperature and the pH on the activity of the GA preparations. Merck soluble starch (Darmstadt, Germany) was used as substrate for this enzymatic hydrolysis. The DNS is prepared according to the following protocol proposed by P. Bernfeld, Methods in enzymology, 1, 149–159 (1955):

Dissolve beforehand:
  10 g of 3,5-dinitrosalicylic acid
  200 ml of 2 molar sodium hydroxide
  200 ml of distilled water.

Then add:
  300 g of sodium potassium tartrate.

Adjust the volume to 1 liter with distilled water after complete dissolution.

Once prepared, this reagent should be stored protected from light. The calibration curves were prepared with glucose as reference product for assaying the glucoamylase activity and for monitoring the liquefaction-saccharification reactions, and with xylose for measuring the xylanase activity.

One glucoamylase activity unit (GU) corresponds to the quantity of enzyme necessary to release one micromole of reducing ends per minute under the assay conditions with glucose as reference. The glucoamylase activity, calculated using the formula indicated below, is expressed relative to the quantity of initial dry matter (IDM):

$$A=(P/Venz)*(Vferm/Mferm)$$

A is the GA activity expressed in $GU.gIDM^{-1}$ ($\mu mol.min^{-1}.gIDM^{-1}$), P is the glucose equivalent release rate in $\mu mol.min^{-1}$, Venz is the volume of the enzyme solution assayed in ml, Vferm is the total volume of distilled water used to extract the enzyme solution in ml, Mferm, expressed in g of IDM, is the initial mass of dry product from which the enzyme solution was extracted.

b) Protease activity

This assay was developed on azocasein using the Béinon method described in "Protein Purification Methods—a Practical Approach", Harris E. L. V. and Angal, S (Editors), IRL-Press, Oxford University Press, 1–66 (1989). The degradation of this substrate by proteases causes the release of azo groups which absorb UV at 340 nm. The variation of the absorbence during the kinetics of hydrolysis of this protein indicates the extent of the reaction.

The reaction medium contains:

| Azocasein solution at 1%, pH 5.0 | 1000 µl |
|---|---|
| Enzyme solution: | 200 µl |

The azocasein (Sigma, Saint-Louis, United States) is dissolved in a 0.1 M acetate buffer at pH 5.0. The protease activities were assayed at this pH because azocasein is insoluble in this acetate buffer at lower pH values. The enzyme reaction is carried out at 60° C. Samples are collected every 5 min for 20 min and mixed with 5% trichloroacetic acid (TCA) to stop the reaction.

One protease activity unit (PU) corresponds to the quantity of enzymes necessary for an increase of 0.01 $A_{340\ nm}$ unit per minute, generated by the release of azo groups under the conditions mentioned above. This activity, calculated based on the formula indicated below, is expressed relative to the initial dry matter ($PU.G^{-1}$ IDM) or the glucoamylase activity ($PU.GU^{-1}$):

$$A=(P/Venz)*(Vferm/Mferm)$$

A is the protease activity expressed in $PU.gIDM^{-1}$,

P is the rate of release of the azo groups expressed as an increase of 0.01 unit $A_{340\ nm}.min^{-1}$, Venz is the volume of the enzyme solution assayed in ml, Vferm is the total volume of distilled water used to extract the enzyme solution in ml, Mferm, expressed in g of IDM, is the initial mass of dry product from which the enzyme solution was extracted.

c) Xylanase activity

To demonstrate this enzyme activity, the GA preparations are reacted with a soluble xylan solution and the reducing sugars released were measured by the DNS method.

The reaction medium is composed of:

| Xylan solution at 1%, pH 4.5: | 900 µl |
|---|---|
| Enzyme solution: | 100 µl |

The solution of larch xylan (Sigma at 1%) is prepared in citrate buffer at pH 4.5 and the reaction occurs at 60° C. Samples are collected every 5 min for 20 min, mixed with DNS and placed in an ice bath. They are then assayed according to a protocol identical to that presented for the measurement of the GA activities with xylose as reference.

One xylanase activity unit (XU) corresponds to the quantity of enzymes necessary for the release of one micromole of reducing sugars per minute. This activity is expresssed relative to the initial dry matter ($XU.g^{-1}$ IDM) or to the glucoamylase activity ($XU.GU^{-1}$). To calculate this activity, the formula defined for the calculation of the GA activities is used again, in which:

A is the xylanase activity expressed in $XU.gIDM^{-1}$ ($\mu mol.min^{-1}.gIDM^{-1}$), P is the rate of release of xylose equivalents in $\mu mol.min^{-1}$, the other terms of the formula are not modified.

The following nonlimiting examples are given to illustrate the invention.

EXAMPLE 1

Selection of Aspergillus Strains

The ability of seven different commercially available Aspergillus strains to produce glucoamylase by solid-state fermentation of wheat bran was studied in a comparative manner.

The trials were carried out on 50 g of fermentation medium in an Erlenmeyer flask. The medium consisted of 21.5 g of wheat bran, 27.5 g of water and 1 g of wheat starch. The initial pH of the medium was 6.0–6.5. The medium was sterilized for 20 min in an autoclave at 120° C.

Each medium was inoculated with $2\times10^7$ spores of the test strain per gram of initial dry matter. The age of the spores was 3 days. The fermentation was allowed to proceed for 40 to 50 hours, and the Erlenmeyer flasks were placed in an oven at 35° C. At the end of fermentation, the fermented medium was mixed with 150 ml of distilled water in order to take the enzymes produced into solution, and the mixture was then filtered to recover the enzyme solution. The solution was centrifuged to remove the residual particles and spores, and the solution was packaged in 100 ml vials which were stored at −20° C. until the glucoamylase activity was analyzed.

The strains tested and the results obtained are summarized in the following table 1:

| Ref. strains from collections | Duration of the SSF (h) | GA Ac. (GU.g$^{-1}$ IDM) |
|---|---|---|
| A. niger ATCC 76060 | 50 | 627 |
| A. niger ATCC 76061 | 50 | 943 |
| A. niger MUCL 28815 | 40 | 710 |
| A. niger MUCL 28816 | 40 | 631 |
| A. niger NRRL 3112 | 50 | 1056 |
| A. oryzae ATCC 22788 | 50 | 903 |
| A. oryzae ATCC 42149 | 50 | 861 |

Note that the A. niger NRRL 3112, A. niger ATCC 76061 and A. oryzae ATCC 226788 strains have the best activities in terms of glucoamylase production.

However, another important property to be taken into consideration is the stability of the glucoamylase produced. Tests of heat-stability were therefore carried out by heat treating enzyme solutions at 55 and 60° C. for 30 min and measuring the glucoamylase activity at the end of this time. These treatments are similar to the conditions of use for the saccharification of starch. It was found that the A. niger ATCC 76061 and A. niger NRRL 3112 strains gave the most stable glucoamylases (100% residual activity after 30 min at 55° C. and about 50% residual activity after 30 min at 60° C.), whereas the A. Oryzae ATCC 22788 and ATCC 42149 strains gave glucoamylases having 0% residual activity after 30 min at 60° C. and 46% residual activity after 30 min at 55° C. The A. niger ATCC 76061 and NRRL 3112 strains were therefore selected. Moreover, the A. niger NRRL 3112 strain proved to be fairly unstable genetically (loss of activity after a few reproductive cycles) and so the most preferred strain is the A. niger ATCC 76061 strain. This strain was therefore used in the subsequent examples.

EXAMPLE 2

Production of glycoamylases in nonsterile 50 l pilot tanks provided by INRA: importance of the pretreatment of wheat bran.

The trials were carried out with a 50 l nonsterile fermentor like that described in the paper by A. DURAND et al., cited above, (FIG. 1 ) and BCE wheat bran (provided by the distillery Brie Champagne Ethanol, Provins, France). Two methods of preparing the bran were used to obtain 5 kg culture medium containing 55% moisture:

dry bran: the bran is autoclaved for 1 h at 105° C. and then mixed with water (trial F4C3);

moist bran: the bran is moistened to 45% in a kneader and autoclaved for 20 min at 121° C. (trial F4C4).

In both cases, inoculation is carried out with $2\times10^7$ spores.g$^{-1}$ DM and the water content of the media is adjusted to about 55%. They are then fermented over a 10 cm bed in aerated tanks. During these cultures, the medium is intermittently streaked using a spatula to reduce its temperature. During the fermentation, the atmosphere is continuously replaced with conditioned air whose temperature, moisture and flow rate are as indicated in the tables.

The results are presented in tables 2 (trial F4C3) and 3 (trial F4C4).

The data makes it possible to draw several conclusions:

Moistening the wheat bran prior to the heat treatment is necessary for an effective production of glucoamylases. Apart from decontamination, heat treatment of the wheat bran probably promotes gelatinization of starch;

The pH appears to be a good qualitative indicator of the variation of growth and of the production of fungal GA, but without making it possible to estimate the quantity of GA obtained:

Moderate stirring of the medium (streaking) does not adversely affect the production of enzymes;

The variation in the water content during these two fermentations indicates considerable drying of the culture medium, which could be damaging to fungal growth.

EXAMPLE 3

Production of glucoamylases in a pilot fermentor provided by the company FUJIWARA: importance of maintaining the moisture content of the medium during fermentation.

This trial was carried out with a pilot fermentor sold by the company FUJIWARA, Okayama, Japan, and BCE wheat bran. It differs in particular from the fermentor used in example 2 in the diameter of the tank, which is 0.66 m against 0.35 m for the INRA tanks. In this fermentor, 20 kg of medium containing 55% water prepared according the moist bran method described in example 2 are necessary to carry out a culture on a thickness of 12 cm. The stirring is provided by three continuously rotating vertical lead screws mixing the medium in the tank under rotation (5–10 min/revolution). During the fermentation, as with the INRA tanks in example 2, the gaseous atmosphere is continuously replaced with conditioned air whose temperature, moisture and flow rate are as indicated in table 4.

During this trial, called FII, the opportunity for regulating moisture content was studied. Localized measurements of the moisture content of the culture, carried out with an infrared apparatus, and of the mass of the medium are used to determine the quantity of water to be added in order to maintain the water content of the medium above 50%.

The results of this FII trial are presented in table 4. The results obtained merit the following comments:

the FII trial clearly indicates that maintaining the water content between 50 and 55% promotes the production of enzymes with 1600 GU/g DM released after 44 h of fermentation, that is more than double the activity obtained during the F4C2 trial of example 2, which did not have this regulation;

stabilizing the production of enzymes from 44 h of culture correlated with the appearance of fungal spores, shows that it is not necessary to continue the culture beyond this phase;

satisfactory regulation of the temperature of the medium at around 35° C. may be obtained by a good combination of conditioning of the air and stirring of the medium;

the culture withstands, with no damage, intermittent mixing performed by the stirring system of the FUJIWARA fermentor.

EXAMPLE 4

Production of glucoamylases in a 50 l stirred INRA pilot fermentor: usefulness of heat pretreatment of the bran with steam and culture under "sterile conditions".

This pilot fermentor is similar to that presented in WO-A-94 18306 and in FIG. 4 of the article by A. DURAND et al. cited above. This tool makes it possible to treat the bran with steam directly in the fermentor, a method of preparation which is preferred at the industrial level. The culture is also prepared, inoculated and carried out under sterile conditions, with the exception of the sample collections, which confers semisterility on this trial and differs from the preceding two examples.

A) Experimental Conditions 9 kg of BCE bran premoistened with 1.5 l of water are introduced into the fermentor and then sterilized in situ for 20 minutes at 121° C., with periodic stirring for 5 seconds every 5 minutes. This treatment makes it possible to reach a moisture level of 46% which is then adjusted to 55% during inoculation.

The bran is inoculated with a koji-type preparation:

180 g of BCE bran (55% initial moisture) fermented for 4 days at 35° C. are mixed with 3 liters of sterilized water to obtain a suspension of spores which constitutes the inoculum.

The initial fermentation conditions are as follows:

18.3 kg of culture with 55% moisture and an initial pH of 5.7;

bed height 40 cm;

aeration rate: 314 l.min$^{-1}$;

temperature of inlet air: 35° C.;

relative humidity of inlet air: 95%.

B) Monitoring Fermentation

In addition to measuring the pH, the temperature of the medium, the percentage of dry matter and the production of GA, the variation in the mass of the culture is continuously recorded on the 50 l stirred fermentor; for the nonsterile reactor, the culture is weighed after 21 h and 42 h of fermentation.

The importance of these measurements of the mass are two-fold:

Maintaining the Moisture During Culture by Estimating the Percentage DM

During fermentation, two phenomena contribute to reducing the mass of the culture; they are:

drying of the medium, which is compensated by supplying water, loss of dry matter, which is linked to the growth of the fungus.

This loss of dry matter is not negligible, 20% DM being lost in 40 h of culture, that is 0.5% DM per hour if linear losses are assumed for the purposes of approximation.

From that, knowing the instantaneous mass of culture $(M_{(t)})$, it is possible to deduce therefrom the theoretical percentage of DM at time t, from the formula:

$$\% \ DM_{theoretical(t)} = \frac{IDM(IDM.0.5) \cdot t}{M_{(t)}}$$

where IDM is the quantity of initial dry matter.

When the % DM calculated in this way exceeds 50%, sterilized water is added to reduce this percentage to 45%.

Expressions of the Results Per Gram of Initial DM

The variations in the mass and the percentage of DM measured make it possible to calculate the loss of real dry matter ($L_{DM}$ expressed in %) during culture. Thus, the quantity of GA expressed thus far in GU.g$^{-1}$ DM may be expressed as GU.g$^{-1}$ initial DM using the following formula:

$$(GU.g^{-1} \ IDM) = GU.g^{-1} \ DM).(100-L_{DM})/100$$

C) Results

Tables 5 and 6 summarize the operating conditions and the results obtained on steam bran in a stirred reactor.

Despite aerating the culture with moisture-saturated air, the drying of the medium is such that it was necessary to readjust its water content when it decreased below 50% on two occasions, as indicated in table 5.

It was possible to maintain the temperature of the medium at an average value of 35° C. by decreasing the inlet air, but in particular by intermittent stirring.

Under these culture conditions, the growth of the fungus, whose progress was monitored by measuring the pH, is maintained for 60 h and makes it possible to reach a production of 1436 GU.g$^{-1}$ DM in 44 h and 1990 GU.g$^{-1}$ DM in 63 h. Expressed relative to the initial DM, the quantity of GA produced is 1160 and 1540 GU.g$^{-1}$ IDM, respectively. For comparison, in the context of example 3, in 44 h of culture, 1605 GU.g$^{-1}$ DM, equivalent to 1067 GU.g$^{-1}$ IDM was obtained. This is advantageous because it indicates that the productivity of these two trials is identical, but that the experimental conditions of example 4 made it possible to prolong the production of enzymes even with a 40 cm bed.

The treatment of the bran with steam followed by fermentation in the 50 l stirred INRA reactor therefore prolongs the fungal culture and the production of enzymes.

Expressed relative to the initial DM, the quantity of GA produced is 1540 GU.g$^{-1}$ IDM.

Assays of xylanase and protease activities were carried out on the same samples. The results obtained are very satisfactory with a maximum, on average, at 50 h of fermentation of 350 XU.g$^{-1}$ IDM for the xylanases;

400 PU.g$^{-1}$ IDM for the proteases.

By virtue of the continuous recording of the mass, it was possible to calculate the loss of dry matter during the culture. It is about 23% after 60 h of culture (to within 2% given the accuracy of weighing).

EXAMPLE 5

Use of the Fermented Brans Produced in Example 4 for the Hydrolysis of Wheat Flours A series of saccharifications with the fermented brans obtained in example 4 was carried out on wheat flours previously subjected to conventional enzymatic liquefaction treatment. The glucoamylase preparation AMG 300L® sold by the company NOVO served as a control. These trials were carried out with a 45-type conventional wheat flour. The operating conditions are summarized in table 7 for 750 g of wort.

TABLE 7

| Product | AMG 300L ® (Novo) | Fermented bran | Dried fermented bran |
|---|---|---|---|
| Reference | AMG 300 L | Ex. 4 | Ex. 4 |
| Presentation | Liquid | Wet bran | Dry bran |
| Preservation method | at +5° C. | at −20° C. | at room T |
| Flour | Commercial type 45 | Commercial type 45 | Commercial type 45 |
| Quantity used (g) | 300 | 300 | 300 |
| Dry matter of the medium (%) | 35 | 35 | 35 |
| Liquefaction cond. | 1 h/88° C./pH 6.1 | 1 h/88° C./pH 6.2 | 1 h/88° C./pH 6.2 |
| Enzyme | 125 µl Termamyl. 120L ® | 125 µl Termamyl. 120L ® | 125 µl Termamyl. 120L ® |
| Saccharif. Cond. | 44 h/58° C./ pH 4.6 | 40 h/58° C./ pH 4.55 | 44 h/60° C./ pH 4.52 |
| Qt. Equiv. to 3500 GU | 205 µl | 4.3 g | 2.1 g |

During these hydrolyses of wheat flour, three samples of medium were collected each time. The results of concentrations of reducing sugars (RS) at various times of the saccharification presented in table 8 are the average of these three samples. These assays, carried out by the DNS technique, were carried out on the supernatants of the centrifuged samples. The final viscosity of the saccharified products was also measured.

TABLE 8

| Measurements | AMG 300L ® (Novo) | Fermented bran | Dried fermented bran |
|---|---|---|---|
| RS conc. (initial (g/l)) | 180.9 ± 4.6 | 185.0 ± 3.1 | 171.5 ± 4.5 |
| Final RS conc. (g/l) | 327.5 ± 18.5 | 325.0 ± 22.5 | 348.3 ± 19.1 |
| Viscosity (mPa.s) | 6.80 | 2.82 | 2.80 |

Moreover, an increase was observed in the soluble nitrogen content of the worts after saccharification due to the proteolytic action of the fermented bran.

These results indicate that the fermented brans produced in example 4 are capable of hydrolyzing wheat flour with the same efficacy as a standard GA preparation, regardless of their method of storage.

The hydrolysis of the flour with fermented bran also results in a notable reduction in viscosity compared with a conventional enzymatic preparation.

EXAMPLE 6

This example illustrates the possibility of producing a considerable quantity of xylanases and a small quantity of glucoamylases with the *Aspergillus niger* strain.

This trial was carried out in a Fujiwara pilot fermentor with BCE bran and an *A. niger* Ref. ATCC 210202 strain known for its capacity to produce xylanases. The operation of the pilot fermentor is described in example 3. 20 kg of medium containing 55% moisture, prepared as in example 2, are used in this example. As in example 3, during the fermentation, the moisture of the medium was maintained above 50% and the temperature of the medium regulated at around 35° C.

After 37 hours under these fermentation conditions, the *A. niger* ATCC 201202 strain produced a fermented bran having 727 XU/g DM and 162 GU/g DM.

EXAMPLE 7

Advantage of incorporating fermented bran according to the invention into a wheat-based poultry feed intended for broilers.

The hemicellulases in wheat flours are known to be partially soluble in water and to increase the viscosity of the intestinal content, thus reducing the release and absorption of nutrients.

It has been demonstrated that the addition of hemicellulases causes degradation of hemicelluloses, thus making it possible to reduce the viscosity of the intestinal content and to improve the zootechnical performance of monogastric animals such as broilers fed with feed in which the only cereal is wheat.

An experiment was carried out on 1200 Ross broilers to show the advantage of using fermented bran carrying hemicellulase (xylanase) activity, compared with feed without enzyme and feed containing a standard source of xylanase, the product Avizyme. Feeds with or without enzyme were prepared so as to feed 4 groups of 300 chicks. Their composition is detailed in table 9. The growth feeds (GR FE) were used for the first 21 days of breeding and were then replaced with finishing feed (FI FE) for 18 days.

TABLE 9

| Feed | GR FE | FI FE |
|---|---|---|
| Moisture (%) | 10.6 | 11.4 |
| Proteins (%) | 21.3 | 19.1 |
| Fatty substances (%) | 6.1 | 6.4 |

Feed 1 received no enzyme. Feeds 2 and 3 were supplemented with 3 and 5 kg, respectively, of fermented bran per ton of feed. Feed 4 was supplemented with 0.6 kg of Avizyme® per ton of feed.

The results of this test after 39 days of breeding are summarized in table 10.

TABLE 10

| Feed | 1 | 2 | 3 | 4 |
|---|---|---|---|---|
| Fermented bran according to the invention (kg/ton)[a] | — | 3.0 | 5.0 | — |
| AVIZYME Finfeed (kg/ton)[b] | — | — | — | 0.6 |
| Xylanase activity (XU/kg feed) | — | 1 700 | 2 840 | 1 620 |
| Feed conversion ratio 39 days[c] | 1.775 | 1.748 | 1.738 | 1.745 |
| Reduction feed conv. ratio (% feed 1)[d] | — | 1.52 | 2.08 | 1.69 |
| Mortality (%) | 2.3 | 2.0 | 3.0 | 2.3 | a. this fermented bran exhibited a glucoamylase activity of 1000 GU/g of dry matter, a proteolytic activity of 125 PU/g of dry matter and a xylanase activity of 600 XU/g of dry matter;
b. Avizyme® is provided by the company Finfeed, Finland;
c. ratio of weight of feed consumed/weight gain;
d. this is the reduction, in %, of the weight of feed consumed relative to the weight of feed 1 (without enzyme) consumed.

The incorporation of fermented bran into a poultry feed (3 or 5 kg/ton) made it possible significantly to reduce the feed conversion ratio. Under the trial conditions, the use of a dose of fermented bran greater than 3 kg/ton appears to be of no practical benefit. The improvements observed are comparable to those obtained with the commercial product Avizyme (0.6 kg/ton). The use of the fermented bran nevertheless has the advantage of being less expensive than the use of the commercial enzymatic product.

It goes without saying that the embodiments described are only examples and they can be modified, in particular by substitution of technical equivalents, without thereby departing from the scope of the invention.

TABLE 5

Physicochemical parameters of the SSF in a 50 l stirred fermentor on its steam

| Cult. Time (t) | Air, inlet T (° C.) | Air, flow rate (1/min) | Air, % RH | Average T medium | Average pH | Total mass | Treatment |
|---|---|---|---|---|---|---|---|
| 0 | 35.0 | 314.0 | 94.6 | | 5.70 | 18.30 | |
| 13 | 36.1 | 312.7 | 92.6 | 38.8 | 4.72 | 18.00 | |
| 13 (after stirring) | | 471.0 | | 38.6 | 4.68 | | stirring |
| 16 | 29.8 | 448.6 | 94.6 | 32.4 | 4.60 | 17.50 | stirring |
| 18 | 33.2 | 466.5 | 77.2 | 31.0 | 4.37 | 17.10 | |
| 20.33 | 32.6 | 466.5 | 93.7 | 34.3 | 4.20 | 16.80 | |
| 23.66 | | | | 34.2 | 4.13 | 15.80 | |
| 26 | 29.8 | 467.5 | 94.6 | 32.9 | 4.17 | 15.10 | |
| 26 | 29.8 | 467.5 | 94.6 | 33.3 | 3.81 | 17.30 | stirring + 2.5 l of water |
| 36.75 | 29.0 | 467.5 | 94.6 | | | | stirring |
| 36.75 | 27.0 | 467.5 | 94.6 | 29.9 | 3.71 | 14.30 | |
| 40.58 | 27.0 | 467.5 | 94.6 | 31.0 | 4.20 | 13.10 | |
| 40.66 | 27.0 | 467.5 | 94.6 | 31.7 | 3.60 | 15.10 | stirring + 2.1 l of water |
| 44.58 | | 448.6 | | 33.6 | 3.71 | 14.10 | |
| 47.17 | | 467.5 | | 34.8 | 4.04 | 13.30 | |
| 50 | 27.0 | 303.3 | 94.6 | 32.0 | 4.09 | 12.80 | stirring |
| 63.33 | 28.7 | 303.0 | | 31.0 | 5.75 | 10.30 | |

TABLE 6

Summary of the results of the SSF on bran treated with steam in a 50 l stirred fermentor

| Cult. Time (h) | Water content (%) | Loss of DM (%) | Loss of DM % (smoothed) | Average GU/g DM | Average GU/g IDM | XU/g DM | XU/g IDM | PU/g DM | PU/g IDM |
|---|---|---|---|---|---|---|---|---|---|
| 0 | 54.50 | −2.07 | | 0.00 | 0.00 | 0.0 | 0.0 | 0.0 | 0.0 |
| 13 | 57.52 | 7.78 | 0.4 | 92.69 | 85.48 | 16.1 | 16.0 | 131.0 | 130.49 |
| 16 | 53.72 | 2.11 | 1.0 | 170.53 | 166.92 | 19.2 | 19.0 | 196.2 | 194.15 |
| 18 | 55.23 | 7.21 | 1.8 | 129.25 | 222.02 | 27.9 | 27.4 | 103.9 | 102.02 |
| 20.33 | 51.90 | 1.91 | 3.1 | 429.36 | 421.18 | 35.0 | 33.9 | 193.7 | 187.63 |
| 23.66 | 50.88 | 5.57 | 5.9 | 551.93 | 521.21 | 51.0 | 48.0 | 283.4 | 266.81 |
| 26 | 49.06 | 6.15 | 8.2 | 651.45 | 611.36 | 75.4 | 69.2 | 296.5 | 272.14 |
| 26 | 57.76 | 10.57 | 8.2 | 548.42 | 490.44 | 54.1 | 49.7 | 262.1 | 240.57 |
| 36.75 | 49.27 | 10.75 | 18.4 | 1127.09 | 1005.88 | 203.5 | 166.2 | 359.1 | 293.20 |
| 40.58 | 51.14 | 20.55 | 20.5 | | | | | | |
| 40.66 | 58.72 | 22.54 | 22.0 | 1278.58 | 990.35 | 227.3 | 180.7 | 347.9 | 276.52 |
| 44.58 | 54.10 | 19.21 | 22.6 | 1436.16 | 1160.27 | 408.3 | 318.6 | 367.1 | 286.45 |
| 47.17 | 54.01 | 23.07 | 23.2 | 1535.69 | 1181.43 | 511.5 | 395.7 | 496.8 | 384.30 |
| 50 | 54.66 | 26.67 | 24.4 | 1742.78 | 1277.91 | 429.8 | 330.1 | 628.2 | 482.48 |
| 63.33 | 44.69 | 22.62 | 22.6 | 1989.07 | 1539.07 | 410.3 | 310.1 | 478.3 | 361.5 |

TABLE 2

| | Cult. Time (h) | Air, inlet T (° C.) | Air, flow rate (1/min) | Air flow rate (m/s) | Air, % RH | Average T medium | Average pH | % moisture | Average GUA/g DM | Cult. Time (h) |
|---|---|---|---|---|---|---|---|---|---|---|
| F4C3 | 0.0 | 35 | 174.4 | 8.0 | 96 | 25.0 | | | | 0.0 |
| dry bran | 3.0 | 35 | 174.4 | 8.0 | 95 | 33.8 | 6.33 | | | 3.0 |
| | 11.0 | 32 | 174.4 | 8.0 | 94 | 34.6 | 5.13 | 54.53 | 20.56 | 11.0 |
| | 14.0 | 30 | 174.4 | 8.0 | 95 | 35.4 | 4.38 | 54.19 | 71.13 | 14.0 |
| streaking (17 h) | 16.0 | 30 | 174.4 | 8.0 | 94 | 33.3 | 4.36 | 52.17 | 123.12 | 16.0 |
| streaking (18 h) | 18.0 | 28 | 174.4 | 8.0 | 92 | 37.4 | 4.51 | 51.31 | 85.78 | 18.0 |
| | 20.0 | 28 | 174.4 | 8.0 | 96 | 31.8 | 3.79 | 49.54 | 132.81 | 20.0 |

TABLE 2-continued

| Cult. Time (h) | Air, inlet T (° C.) | Air, flow rate (1/min) | Air flow rate (m/s) | Air, % RH | Average T medium | Average pH | % moisture | Average GUA/g DM | Cult. Time (h) |
|---|---|---|---|---|---|---|---|---|---|
| 22.0 | 28 | 174.4 | 8.0 | 95 | 34.7 | 4.12 | 45.17 | 188.0 | 22.0 |
| 25.0 | 28 | 174.4 | 8.0 |  | 37.6 | 4.34 | 45.13 | 181.03 | 25.0 |
| 28.0 | 28 | 174.4 | 8.0 | 94 | 32.6 | 4.63 | 36.47 | 129.58 | 28.0 |
| 31.0 | 28 | 174.4 | 8.0 |  | 32.8 | 5.05 | 30.68 | 198.10 | 31.0 |
| 40.0 | 28 | 174.4 | 8.0 | 95 | 31.9 | 5.69 | 23.96 | 246.86 | 40.0 |

TABLE 3

| | Cult. Time (h) | Air, inlet T (° C.) | Air, flow rate (1/min) | Air flow rate (m/s) | Air, % RH | Average T medium | Average pH | % moisture | Average GUA/g DM | Cult. Time (h) |
|---|---|---|---|---|---|---|---|---|---|---|
| F4C4 | 0.0 | 35 | 174.4 | 8.0 | 96 | 25.0 | 5.96 |  |  | 0.0 |
| dry bran | 3.0 | 35 | 174.4 | 8.0 | 95 | 33.8 | 6.12 |  |  | 3.0 |
|  | 11.0 | 32 | 174.4 | 8.0 | 94 | 35.1 | 5.06 | 53.93 | 135.77 | 11.0 |
| streaking (14 h) | 14.0 | 30 | 174.4 | 8.0 | 95 | 39.9 | 4.66 | 53.04 | 121.02 | 14.0 |
|  | 16.0 | 30 | 174.4 | 8.0 | 94 | 33.1 | 4.59 | 51.53 | 182.96 | 16.0 |
| streaking (18 h) | 18.0 | 28 | 174.4 | 8.0 | 92 | 38.0 | 4.48 | 50.80 | 327.41 | 18.0 |
|  | 20.0 | 28 | 174.4 | 8.0 | 96 | 34.3 | 3.72 | 51.76 | 360.25 | 20.0 |
|  | 22.0 | 28 | 174.4 | 8.0 | 95 | 36.9 | 3.70 | 47.65 | 618.00 | 22.0 |
|  | 25.0 | 28 | 174.4 | 8.0 |  | 36.3 | 4.15 | 41.68 | 658.05 | 25.0 |
|  | 28.0 | 28 | 174.4 | 8.0 | 94 | 30.9 | 4.53 | 35.73 | 660.03 | 28.0 |
|  | 31.0 | 28 | 174.4 | 8.0 |  | 30.8 | 5.18 | 33.98 | 583.62 | 31.0 |
|  | 40.0 | 28 | 174.4 | 8.0 | 95 | 30.2 | 4.88 | 30.02 | 702.74 | 40.0 |

TABLE 4

| | Time (h) | Rate of ventilation rev./min | Moisture air (%) | T ° C. air inlet | T ° C. medium | Moisture medium % | pH | GU/g DM | GU/g IDM | Time (h) |
|---|---|---|---|---|---|---|---|---|---|---|
| stirring | 0 | 15 | 99.0 | 35.0 | 25.0 | 54.0 | 6.36 | 4.3 | 4.3 | 0 |
|  | 10 | 15 | 98.5 | 35.0 | 34.7 | 53.7 | 5.95 | 23.9 |  | 10 |
|  | 12 |  |  | 33.0 |  |  |  |  |  | 12 |
|  | 15 | 15 | 98.6 | 33.0 | 34.5 | 51.6 | 4.92 | 133.3 |  | 15 |
| stirred + 3 1 of water | 18 | 15 | 98.8 | 33.0 | 37.3 | 49.7 | 4.18 | 304.8 | 273.1 | 18 |
|  | 21 | 15 | 98.3 | 30.0 | 30.7 | 54.7 | 3.83 | 472.1 |  | 21 |
|  | 24 | 15 | 98.2 | 30.0 | 31.9 | 52.4 | 3.76 | 709.2 |  | 24 |
| stirred + 2 1 of water | 28 | 15 | 97.9 | 30.0 | 33.4 | 46.6 | 4.08 | 1198.0 |  | 28 |
|  | 29 | 25 | 98.0 | 30.0 |  | 51.6 |  | 1054.0 |  | 29 |
| stirred + 6 1 of water | 38 | 15 | 98.6 | 32.0 | 31.5 | 39.2 | 5.00 | 1469.7 | 976.1 | 38 |
|  | 39 | 15 | 99.0 | 32.0 |  | 60.6 |  | 1338.0 |  | 39 |
|  | 42 | 15 | 99.2 | 32.0 | 33.9 | 59.7 | 5.28 | 1514.8 |  | 42 |
|  | 44 | 15 | 98.1 | 32.0 | 34.1 | 54.8 | 5.76 | 1605.1 | 1067.6 | 44 |
|  | 46 | 15 | 96.8 | 32.0 | 33.7 | 52.6 | 6.33 | 1601.0 |  | 46 |
|  | 66 | 15 | 99.0 | 32.0 | 32.4 | 34.0 | 7.28 | 1594.4 | 1161.7 | 66 |

What is claimed is:

1. A multi-enzyme product consisting essentially of wheat bran fermented by an *Aspergillus niger* strain and exhibiting:

a glucoamylase of at least 100 GU per gram of dry matter, a proteolytic activity of at least 100 PU per gram of dry matter, and a xylanase activity of at least 100 XU per gram of dry matter, provided that at least one of the following conditions is satisfied:

the glucoamylase activity is at least 750 GU per gram of dry matter, the xylanase activity is at least 300 XU per gram of dry matter.

2. The multi-enzyme product of claim 1, wherein the glucoamylase activity is at least 750 GU/g of dry matter.

3. The multi-enzyme product of claim 1, wherein the glucoamylase activity is at least 1,500 GU/g of dry matter.

4. The multi-enzyme product of claim 1, wherein the xylanase activity is at least 300 XU per gram of dry matter.

5. The multi-enzyme product of claim 1, wherein the xylanase activity is at least 400 XU per gram of dry matter.

6. The multi-enzyme product of claim 1, wherein the *Aspergillus niger* strain is NRRL 3112 or ATCC 76061.

7. The multi-enzyme product of claim 6, wherein the *Aspergillus niger* strain is ATCC 76061.

8. A method for producing the multi-enzyme product of claim 1, which comprises (a) moistening the wheat bran and then heat-treating the wheat bran;
(b) inoculating the heat-treated wheat bran with an *Aspergillus niger* strain;
(c) laying the wheat bran in the form of a layer of at least 10 cm thick;
(d) fermenting the wheat bran in the solid state in a reactor for a period of 1 to 3 days at a temperature of 28–38° C.;
(e) adjusting the moisture content of the wheat bran to 50 to 60 wt. %;
(f) maintaining the moisture content of the wheat bran between 50 to 60 wt. % during the fermentation step;
(g) periodically stirring the wheat bran; and
(h) periodically aerating the wheat bran in order to avoid accumulation of carbon dioxide and a rise in temperature above 38° C.

9. The method of claim 8, wherein the *Aspergillus Niger* strain is NRRL 3112 or ATCC 76061.

10. The method of claim 9, wherein the *Aspergillus niger* strain is ATCC 76061.

11. The method of claim 8, and further comprising preventing the moisture level of the wheat bran from falling below 45% during the fermentation step.

12. The method of claim 8, and further comprises freezing or drying the layer of step (c).

13. An enzymatic method for producing ethanol from wheat which comprises liquefying a wheat starch or a wheat flour and then adding the multi-enzyme product of claim 1.

14. A monogastric animal feed additive comprising the multi-enzyme product of claim 1.

15. A method of improving the zootechnical performance of a monogastric animal which comprises administering to the animal the multi-enzyme product of claim 1.

* * * * *

UNITED STATES PATENT AND TRADEMARK OFFICE
CERTIFICATE OF CORRECTION

PATENT NO.     : 6,667,066 B2
DATED          : December 23, 2003
INVENTOR(S)    : Labeille et al.

It is certified that error appears in the above-identified patent and that said Letters Patent is hereby corrected as shown below:

<u>Title page,</u>
Item [57], ABSTRACT,
Line 10, "gluycoamylase" should be replaced by -- glucoamylase --

<u>Column 5,</u>
Line 10, "orizae" should be replaced by -- oryzae --

<u>Column 7,</u>
Line 33, "ATCC 226788" should be replaced by -- ATCC  22  788 --

<u>Column 8,</u>
Line 20, "pII" should be replaced by -- pH --

<u>Column 10,</u>
Line 2, "0.5" should be replaced by -- 0.5% --

<u>Column 11,</u>
Line 60, "ATCC 210202" shuold be replaced by -- ATCC  201  202 --

Signed and Sealed this

Seventeenth Day of August, 2004

JON W. DUDAS
*Acting Director of the United States Patent and Trademark Office*